US006730295B2

(12) United States Patent
Fitzpatrick et al.

(10) Patent No.: US 6,730,295 B2
(45) Date of Patent: May 4, 2004

(54) ANIONIC POLYMERS AS SPECIES SPECIFIC ANTIBACTERIAL AGENTS

(75) Inventors: Richard J. Fitzpatrick, Marblehead, MA (US); Robert H. Barker, Jr., Canton, MA (US)

(73) Assignee: Genzyme Corporation, Waltham, MA (US)

( * ) Notice: Subject to any disclaimer, the term of this patent is extended or adjusted under 35 U.S.C. 154(b) by 348 days.

(21) Appl. No.: 09/847,053

(22) Filed: May 1, 2001

(65) Prior Publication Data

US 2002/0034491 A1 Mar. 21, 2002

Related U.S. Application Data

(60) Provisional application No. 60/201,517, filed on May 2, 2000.

(51) Int. Cl.[7] .............................................. A61K 31/74
(52) U.S. Cl. ............................... 424/78.28; 424/78.08; 424/78.17; 424/78.27
(58) Field of Search ......................... 424/78.08, 78.17, 424/78.18, 78.27, 78.28

(56) References Cited

U.S. PATENT DOCUMENTS

| | | | |
|---|---|---|---|
| 3,224,941 A | 12/1965 | Nosh et al. ................... 167/55 |
| 3,466,365 A | 9/1969 | Schlesinger .................. 424/78 |
| 3,987,163 A | 10/1976 | Rankin ........................ 424/78 |
| 4,362,711 A | 12/1982 | Cerami ........................ 424/33 |
| 4,395,392 A | 7/1983 | Wolgemuth .................. 424/78 |
| 5,071,759 A | 12/1991 | Rothman et al. ............ 435/240 |
| 5,093,130 A | 3/1992 | Fujii et al. ................... 424/463 |
| 5,128,323 A | 7/1992 | Pranger ....................... 514/23 |
| 5,149,523 A | 9/1992 | Lundberg et al. .......... 424/78.1 |
| 5,149,543 A | 9/1992 | Cohen et al. ................ 424/499 |
| 5,171,738 A | 12/1992 | Kodama et al. .......... 424/78.17 |
| 5,231,003 A | 7/1993 | Coughlin et al. ........... 435/7.32 |
| 5,277,820 A | 1/1994 | Ash ............................. 210/646 |
| 5,308,701 A | 5/1994 | Cohen et al. ........... 428/402.22 |
| 5,324,718 A | 6/1994 | Loftsson ....................... 514/58 |
| 5,435,821 A | 7/1995 | Duvdevani et al. ............ 71/28 |
| 5,474,765 A | 12/1995 | Thorpe .................... 424/178.17 |
| 5,484,773 A | 1/1996 | Heerze et al. ................ 514/23 |
| 5,601,823 A | 2/1997 | Williams et al. .......... 424/167.1 |
| 5,610,023 A | 3/1997 | Deutsch ..................... 435/7.32 |
| 5,614,559 A | 3/1997 | Singh et al. ................. 514/577 |
| 5,618,825 A | 4/1997 | Baldwin et al. ............. 514/317 |
| 5,635,606 A | 6/1997 | Heerze et al. ............... 530/412 |
| 5,643,562 A | 7/1997 | Kisilevsky et al. ....... 424/78.31 |
| 5,677,343 A | 10/1997 | Singh et al. ................. 514/577 |
| 5,679,775 A | 10/1997 | Boos et al. .................. 530/351 |
| 5,736,139 A | 4/1998 | Kink et al. ................ 424/164.1 |
| 5,762,934 A | 6/1998 | Williams et al. .......... 424/157.1 |
| 5,773,000 A | 6/1998 | Bostwick et al. ......... 424/167.1 |
| 5,800,803 A | 9/1998 | Mirajkar et al. .............. 424/54 |
| 6,007,803 A | 12/1999 | Mandeville, III et al. .. 424/78.1 |
| 6,060,235 A | 5/2000 | Neenan et al. .................. 435/5 |
| 6,075,050 A | 6/2000 | Singh et al. ................. 514/517 |
| 6,270,755 B1 * | 8/2001 | Bacon Kurtz et al. ... 424/78.08 |
| 6,290,946 B1 * | 9/2001 | Kurtz et al. .............. 424/78.08 |
| 6,419,914 B2 * | 7/2002 | Kurtz et al. .............. 424/78.08 |
| 6,517,826 B1 * | 2/2003 | Kurtz et al. .............. 424/78.08 |
| 6,517,827 B1 * | 2/2003 | Bacon Kurtz et al. ... 424/78.08 |

FOREIGN PATENT DOCUMENTS

| | | |
|---|---|---|
| CA | 1114997 | 12/1981 |
| EP | 0 671 162 A2 | 8/1990 |
| EP | 0 579 435 A1 | 7/1993 |
| EP | 0 800 862 A1 | 10/1997 |
| FR | 2 669 535 | 11/1990 |
| GB | 1 466 702 | 2/1974 |
| JP | 19870178097 | 1/1989 |
| WO | WO 93/05816 | 4/1993 |
| WO | 93/14146 | 7/1993 |
| WO | WO 98/12203 | 3/1998 |
| WO | 99/20285 | 4/1999 |

OTHER PUBLICATIONS

Higaki, M., et al., "Enhancement of Immune Response to Intranasal Influenza HA Vaccine by Microparticle Resin", *Vaccine* 16 (7) :741–745 (1998).

DeRosa, A., et al., "Effects of Sodium Polystyrene Sulfonate on Gingival Plaque: Microbiological Investigation and Clinical Follow–Up", *Microbiologica* 19:357–362 (1996).

Carson, D.L., et al., "Ocular Toxicity of Ciprofloxacin/PSSA Fluoroquinolone Antibacterial Solution in Pigmented Rabbits", *J. Toxicol.—Cut. & Ocular Toxicol.* 15 (2) :165–178 (1996).

Moreau, J.M., et al., "Effectiveness of Ciprofloxacin–Polystyrene Sulfonate (PSS), Ciprofloxacin and Ofloxacin In A Staphylococcus Keratitis Model" (Abstract), *Current Eye Research* 17 (8) :808–812 (1998).

Engel, L.S., "The Effectiveness of Two Ciprofloxacin Formulations for Experimental Pseudomonas and Staphylococcus Keratitis", *Jpn J. Opthalmol.*, 40 (2) :212–219 (1996).

Zeitlin, L., et al., "Tests of Vaginal Microbicides in the Mouse Genital Herpes Model", *Contraception*, 56:329–335 (1997).

Rashid, A., et al., "Necrosis of the Gastrointestinal Tract in Uremic Patients as a Result of Sodium Polystyrene Sulfonate (Kayexalate) in Sorbitol", *American J. of Surgical Pathology*, 21(1):60–69 (1997).

Gerstman, B., et al., "Intestinal Necrosis Associated with Postoperative Orally Administered Sodium Polystyrene Sulfonate in Sorbitol", *Am. J. of Kidney Diseases*, 20(2):159–161 (1992).

Linakis, J.G., et al., "Multiple–Dose Sodium Polystyrene Sulfonate in Lithium Intoxication: An Animal Model", *Pharmacology & Toxicology*, 70:38–40 (1992).

Mohan, P., et al., "Sulfonic Acid Polymers as a New Class of Human Immunodeficiency Virus Inhibitors", *Antiviral Research*, 18:139–150 (1992).

(List continued on next page.)

*Primary Examiner*—Thurman K. Page
*Assistant Examiner*—Konata M. George
(74) *Attorney, Agent, or Firm*—Hamilton, Brook, Smith & Reynolds, P.C.

(57) ABSTRACT

The present invention relates to the discovery that certain anionic polymers have useful antibacterial activity.

12 Claims, No Drawings

OTHER PUBLICATIONS

Taylor, N.S., et al., "Binding of Clostridium Difficile Cytotoxin and Vancomycin by Anion–Exchange Resins", *J. of Infectious Diseases,* 141(1):92–97 (1980).

Burbige, E.J., et al., "Pseudomembranous Colitis", *JAMA,* 231(11):1157–1158 (1975).

Lipman, N.S., et al., "Utilization of Cholestyramine Resin as a Preventive Treatment for Antibiotic (Clindamycin) Induced Enterotoxaemia in the Rabbit", *Laboratory Animals,* 26:1–8 (1992).

Bartlett, J.G., et al., "Anion–Exchange Resins in Antibiotic–Associated Colitis," *The Lancet,* 258–259 (1978).

Tedesco, F.J., "Treatment of Recurrent Antibiotic–Associated Pseudomembranous Colitis", *Am. J. of Gastroenterology,* 77(4):220–221 (1982).

Itoh, et al. "Suppression of Influenza Virus Infection by an N–Thioacetylneuraminic Acid Acrylamide Copolymer Resistant to Neurominidase." *Virology,* 212:340–347 (1995).

Vogl, O., et al., "Functional Polymers with Biologically Active Groups." *J. of Macromol. Sci. —Chem.,* A13 (3):415–439 (1979).

Regelson, W. "The Antimitotic Activity of Polyanions." *Advances in Chemotherapy,* 3:303–371 (1968).

* cited by examiner

ANIONIC POLYMERS AS SPECIES SPECIFIC ANTIBACTERIAL AGENTS

RELATED PARAGRAPHS

This application claims the benefit of U.S. Provisional Application No. 60/201,517, filed on May 2, 2000. The entire teachings of which are incorporated herein by reference.

BACKGROUND OF THE INVENTION

The development of antimicrobial chemotherapeutic agents has significantly reduced the morbidity and mortality associated with bacterial infections over the last century, particularly in developed countries. However, the emergence of drug-resistant bacterial strains threatens the resurgence of diseases long thought to have been conquered. For example, a growing number of cases of drug-resistant tuberculosis have been reported since the mid-1980s, and a recent increase in multiple drug resistant *Staphylococcus aureus* infections has been observed. As the prevalence of drug-resistant bacteria increases, there is a growing need for new antibacterial agents which are suitable for use against a variety of bacterial targets.

SUMMARY OF THE INVENTION

The present invention relates to the discovery that certain anionic polymers have useful antibacterial activity.

In one embodiment, the invention provides a method of treating a bacterial infection in a patient. The method comprises the step of administering to the patient a therapeutically effective amount of a polymer selected from the group consisting of poly(undecenesulfate), poly(undecenephosphate), poly(undecenesulfonate), poly(styrenesulfonate), poly(undecenoic acid-co-undecenesulfate) and poly(monoalkylmaleic acid).

The invention further relates to pharmaceutical compositions comprising one or more polymers comprising pendant anionic groups in a therapeutically effective amount.

DETAILED DESCRIPTION OF THE INVENTION

The present invention relates to a method of treating a bacterial infection in a patient, for example, a mammal, such as a human, by administering to the patient a therapeutically effective amount of a polymer selected from poly(undecenesulfate), poly(undecenephosphate), poly(undecenesulfonate), poly(styrenesulfonate), poly(undecenoic acid-co-undecenesulfate) and poly(monoalkylmaleic acid), copolymers or pharmaceutically acceptable salts thereof.

The polymer can be administered in the acid form, in which 0–100% of the acidic groups are protonated, or in the conjugate base form, wherein 0–100% the acidic functional groups are deprotonated and carry a negative charge. In the conjugate base form, the negative charge of the polymer is balanced by a suitable number of counter cations, such as alkali metal ions, for example, sodium, potassium or cesium ions; alkaline earth metal ions, such as magnesium ions or calcium ions; transition metal ions; or substituted or unsubstituted ammonium, (tetraalkylammonium ions, for example). In one embodiment, the cation is a polyvalent metal ion, such as $Ca^{2+}$, $Mg^{2+}$, $Zn^{2+}$, $Al^{3+}$, $Bi^{3+}$, $Fe^{2+}$ or $Fe^{3+}$.

As used herein, a "therapeutically effective amount" is an amount sufficient to inhibit or prevent, partially or totally, a bacteral infection or to reverse the development of a bacterial infection or prevent or reduce its further progression.

The polymer to be administered will, preferably, be of a molecular weight which is suitable for the intended mode of administration and allows the polymer to reach and remain (to the extent and duration necessary) within the targeted region of the body. For example, a method for treating an intestinal infection can utilize a polymer of sufficiently high molecular weight to resist absorption, partially or completely, from the gastrointestinal tract into other parts of the body. The polymers can have molecular weights ranging from about 1 to about 1 million Daltons or more, such as about 500 or about 2,000 Daltons to about 500,000 Daltons, about 5,000 Daltons to about 150,000 Daltons or about 25,000 Daltons to about 1 million Daltons.

In a preferred embodiment, the polymer to be administered is selected from the group consisting of poly(undecenesulfate), poly(undecenephosphate), poly(undecene-sulfonate), poly(styrenesulfonate), poly(undecenoic acid-co-undecenesulfate) and poly(monoalkylmaleic acid), where the alkyl group is a linear or branched $C_2$–$C_{12}$-alkyl group. The polymers can include copolymers, such as polymers manufactured by copolymerizing an alkyl-substituted vinyl (e.g., a $C_2$–$C_{12}$ alkyl, such as styrene.

The bacterial infection is, preferably, an infection by a bacterial species selected from the group consisting of Neisseria species, such as *Neisseria meningitidis* and Branhamella species, such as *Branhamella catarrhalis*. The infection can be a systemic infection or a localized infection. Preferably, the infection is localized to one or more of the oral cavity, the eye, the gastrointestinal tract, including the throat and colon, the skin and the ear, such as the ear canal or the middle ear.

In one embodiment, the bacterial infection is an infection by *Streptococcus sanguis* and the polymer which is administered is poly(styrene sulfonate), poly(undecenesulfate) or poly(undecenesulfonate). The poly(styrene sulfonate) is preferably administered in the anionic form in combination with a suitable cation, as described above. For example, the polymer which is administered can be poly(styrene sulfonate, $Na^+$).

In yet another embodiment, the bacterial infection is an infection by *Neisseria meningitidis* and the polymer to be administered is poly(styrene sulfonic acid); poly(styrene sulfonate), poly(undecenesulfonate), poly(undecenesulfate), poly(undecenoic acid-co-undecenesulfate) or poly(monoalkylmaleic acid), where the alkyl group is a linear or branched $C_2$–$C_{12}$-alkyl group, preferably a decyl group.

In a further embodiment, the infection is an infection by *Branhamella catarhallis* (formerly,*Moraxella catarhallis*), and the polymer which is administered is poly(styrenesulfonate), poly(styrenesulfonic acid), poly(undecenoic acid), poly(undecenesulfate) and poly(undecenoic acid-co-undecenesulfate).

The quantity of a given polymer to be administered will be determined on an individual basis and will be determined, at least in part, by consideration of the individual's size, the severity of symptoms to be treated and the result sought. The polymer can be administered alone or in a pharmaceutical composition comprising the polymer, one or more acceptable carriers or diluents and, optionally, one or more additional drugs, such as antibiotics, antiinflanmuatory agents or analgesia.

The polymer can be administered systemically or non-systemically, for example, by subcutaneous or other injection, intravenously, topically, orally, parenterally, transdermally, or rectally. The route of administration selected will generally depend upon whether the infection is systemic or localized. The form in which the polymer will be administered, for example, powder, tablet, capsule, solution, or emulsion, will depend on the route by which it is administered. The therapeutically effective amount can be administered in a single dose or a series of doses separated by appropriate time intervals, such as hours. Preferably, the polymer is administered non-systemically, for example, orally or topically, for example, by application to the skin, the eye, oral tissue, such as the oral mucosa, or gastrointestinal mucosa.

The polymers of this invention can be administered to the patient by themselves or in pharmaceutical compositions in which they are mixed with one or more suitable carriers and/or excipients at doses to sufficient to treat the microbial infection. Mixtures of these compounds can also be administered to the patient as a simple mixture or in suitable formulated pharmaceutical compositions. Techniques for formulation and administration of the compounds of the instant application are known in the art and can be found, for example, in "Remington: the Science and Practice of Pharmacy," $19^{th}$ edition, Mack Publishing Co., Easton, Pa. (1995).

The polymers of use in the present method are preferably substantially non-biodegradable and non-absorbable. That is, the polymers do not substantially break down under physiological conditions into fragments which are absorbable by body tissues. The polymers preferably have a non-hydrolyzable backbone, which is substantially inert under conditions encountered in the target region of the body, such as the gastrointestinal tract.

The polymer can be crosslinked, for example, by the incorporation within the polymer of a multifunctional comonomer. Suitable multifunctional co-monomers include diacrylates, triacrylates and tetraacrylates, dimethacrylates, diacrylamides, diallylacrylamide, di(methacrylamides), and triallylamine. Specific examples include ethylene glycol diacrylate, propylene glycol diacrylate, butylene glycol diacrylate, ethylene glycol dimethacrylate, butylene glycol dimethacrylate, methylene bis(methacrylamide), ethylene bis(acrylamide), ethylene bis(methacrylamide), ethylidene bis(acrylamide), ethylidene bis(methacrylamide), pentaerythritol tetraacrylate, trimethylolpropane triacrylate, bisphenol A dimethacrylate, and bisphenol A diacrylate. Other suitable multifunctional monomers include polyvinylarenes, such as divinylbenzene.

The polymer can also be cross-linked subsequent to polymerization. For example, a portion of the acid functional groups can be converted to a reactive derivative, as is known in the art. For example, carboxylic acid and sulfonic acid groups react with thionyl chloride to produce, respectively, acyl chloride and sulfonyl chloride groups. These reactive groups can then be reacted with a diamine, a dialcohol or an amino alcohol, preferably diamine, a dialcohol or an amino alcohol in which the amino and/or hydroxyl groups are separated by an alkylene chain, such as a $C_3$–$C_{18}$-alkylene chain. This reaction results in the formation of ester and/or amide groups on a given polymer chain which are linked to similar groups on adjacent polymer chains. The extent of cross-linking can be controlled, for example, by controlling the fraction of acid functional groups which are converted to reactive groups.

The amount of crosslinking agent is typically between about 1.0% and about 30% by weight relative to the weight of the polymer, preferably from about 5% to about 25% by weight.

The polymer or polymers comprising pendant acid functional groups can be administered alone or in combination with one or more additional therapeutic agents, for example, one or more antimicrobial agents, such as those known in the art. For example, the polymer or polymers can be administered in combination with one or more agents, such as antimicrobial agents, which can be employed in the treatment of the particular microbial infection. Suitable antimicrobial agents are known in the art and include isoniazid, rifampin, pyrazinamide, ethambutol, erythromycin, vancomycin, tetracycline, chloramphenicol, ampicillin, cephalosporins, sulfonamides, gentamicin, amoxicillin, penicillin, streptomycin, p-aminosalicyclic acid, clarithromycin, clofazimine, minocycline, ethionamide, cycloserine, kanamycin, amikacin, capreomycin, viomycin, thiacetazone, rifabutin and the quinolones, such as ciprofloxacin, ofloxacin and sparfloxicin.

The term "antimicrobial agent" is intended to include antibacterial agents, antifungal agents, antiseptics and the like. Suitable antimicrobial agents are known in the art and include "Antibacterial agents" include but is not limited to: naturally occurring antibiotics produced by microorganisms to suppress the growth of other microorgansims, and agents synthesized or modified in the laboratory which have either bactericidal or bacteriostatic activity, e.g., $\mu$lactam antibacterial agents including, e.g. carbencillim; ampicillin, cloxacillin, oxacillin and pieracillin, cephalosporins and other cephems including, e.g. cefaclor, cefamandole, cefazolin, cefoperazone, ceftaxime, cefoxitin, ceftazidime, ceftriazone and carbapenems including, e.g., imipenem and meropenem; and glycopeptides, macrolides, quinolones (e.g. nalidixic acid), tetracyclines, aminoglycosides (e.g. Gentamicin and Paromomycin) and further includes antifungal agents. In general if an antibacterial agent is bacteriostatic, it means that the agent essentially stops bacterial cell growth (but does not kill the bacteria); if the agent is bacteriocidal, it means that the agent kills bacterial cells (and may stop growth before killing the bacteria).

If two or more polymers of the invention are administered in combination, they can be administered simultaneously, sequentially or separately, for example, with administration of each compound or two or more groups of compounds separated by a suitable time interval, such as hours. When the polymer or polymers of the invention are administered in combination with one or more additional agents, such as are discussed above, the compound or compounds of the invention and the additional agent or agents can be administered simultaneously, sequentially or separately, for example, with administration of each agent or two or more groups of agents separated by a suitable time interval, such as hours.

The invention will now be further and specifically described by the following examples.

EXAMPLES

Example 1—Preparation of Sulfonated Polystyrene Gels

Polystyrene gels were prepared by polymerizing styrene with divinyl benzene in toluene using about 1 mole % AIBN as initiator as follows:

Polystyrene gel (6% DVB). Styrene (282 mmole, 3.23 mL) was added to a 40 mL vial fitted with a septum cap. Toluene (5 mL) was added and the solution was degassed for 15 min. A solution of AIBN (0.9852 g in 10 mL of toluene) was prepared and 0.5 mL was added to the solution. The solution was further degassed for 5 min and then maintained at 60° C. for 21 hr. The resulting clear colorless gel was washed 5 times with ethanol in a 50 mL centrifuge tube and dried overnight in a 70° C. forced air oven.

Polystyrene gels were also prepared using this procedure with the following cross-linking levels: 4% DVB; 2% DVB; 1.5% DVB; 1% DVB; and 0.5% DVB.

Sulfonation of Polystyrene Gel

Dried polystyrene gel was transferred to a 40 mL glass vial. Concentrated sulfuric acid (10 mL) was added and the mixture was heated at 100° C. for 1 hr. The resulting brown, swollen gel was allowed to cool to room temperature and was washed exhaustively with methanol until the pH was 4–5. The gel was dried overnight in a 70° C. forced air oven. The dried gel was then ground in a coffee grinder, transferred to a 50 mL centrifuge tube, and washed several times with water.

Example 2 —Synthesis of Poly(styrenesulfonate) Calcium Salt

To a 500 mL 3-necked round bottomed flask were added 2 g of poly(sodium 4-styrene sulfonate) and 100 mL of deionized water. The mixture was stirred for several minutes until a homogeneous solution was obtained. To this polymer solution was added 6.46 mL of a 0.225 M solution of $CaCl_2$. The reaction mixture was allowed to stir at room temperature for 15 hr.

The reaction mixture was purified by membrane centrifugation using molecular weight 3K cut-off filters. The solution was dried at 70° C. in a forced air oven for 24 hours, yielding 1.4 g of the polymer as an off white solid.

Example 3—Preparation of Cross-linked Styrenesulfonate Copolymers with Hydrophobic Co-monomers Polystyrenesulfonate Gel (2% cross-linked)

Polystyrenesulfonate (29.4 mmoles, 5.119 g) and divinylbenzene (0.6 mmoles, 85.5 microL) were dissolved in 10 mL ethanol and 10 mL water in a 40 mL vial fitted with a septum cap. The solution was degassed by bubbling nitrogen through and 1 mole % AIBN was added as a solution. The polymerization solution was further degassed and the placed in a heated reaction block at 60° C. for 18 h. A clear, colorless gel formed.

Polystyrenesulfonate-co-styrene Gel (75 mole %:23 mole %:2% cross-linked)

Polystyrenesulfonate (22.5 mmoles, 3.918 g), styrene (6.90 mmoles, 0.7906 mL), and divinylbenzene (0.6 mmoles, 85.5 microL) were dissolved in 10 mL ethanol and 10 mL water in a 40 mL vial fitted with a septum cap. The solution was degassed by bubbling nitrogen through and 1 mole % AIBN was added as a solution. The polymerization solution was further degassed and the placed in a heated reaction block at 60° C. for 18 h. A clear, colorless gel formed.

Example 4—Effect of Variation of Anionic Groups on Bacterial Activity.

The minimum inhibitory concentration (MIC) assay is performed according to the Performance Standards for Antimicrobial Susceptibility Testing, 1998, vol. M 100-S8, Eighth Informational Supplement, NCCLS, 940 West Valley Road, Suite 1400, Wayne, Pa. 19087.

Polymers to be tested were dissolved in 0.85% saline to a final concentration of either 830 or 1000 µg/ml, the pH was adjusted to 7.0 and the solution was filter-sterilized through a 0.22 µm filter. Two-fold serial dilutions of polymer were prepared in Mueller-Hinton broth with cations aliquotted into 96-well microtiter plates. The plates were then inoculated with 5×1 cells/ml of target organism, and incubated 18–24 hr at 35° C. The optical density (OD) was then read at 590 nm, and microorganism growth was scored (OD >0.1 is considered to be growth; OD <0.1 is considered growth inhibition). The MIC value was defined as the lowest concentration of compound which inhibits growth.

Results

The results of the assay are shown below for a variety of acid-functionalized polymers. Poly(undecenesulfate) (sodium salt) was very active against all Neisseria, and Branhamella, but no other pathogens. Two copolymers that contained the undecenesulfate monomer, were also active only against these same pathogens. If the sulfate group were replaced with a phosphate group, then the polymer was active only against S. sanguis. If the sulfate group were replaced with a sulfonate group, then the polymer was slightly less active against the Neisseria and Streptococcus, but completely inactive against Branhamella. If the sulfate group were replaced with a carboxylate group, then the polymer was inactive against all pathogens tested. These examples demonstrate some of the specific antibacterial activity that can be attained by varying the anionic group on the polymer.

Not only is the nature of the anionic group important to activity, but the polymer backbone is also crucial. Poly(undecenesulfate) is very active against Neisseria and Branhamella. However, dextran sulfate and poly(vinylsulfate) are completely inactive against these pathogens.

Sulfonated poly(styrene) (sodium salt) was active against Neisseria, and Branhamella. Against Branhamella, significant activity is achieved with a Mw of 400,000–500,000; activity decreases with increasing or decreasing Mw.

TABLE 1

| polymer | Bacterial species* | | | | | |
|---|---|---|---|---|---|---|
| | 1 | 2 | 3 | 4 | 5 | 6 |
| poly(4-styrene sulfonate, Na=) Mw = 123,900 | >83 | >83 | >83 | >83 | 9 | 28 |
| poly(4-styrene sulfonate, Na+) Mn = 321,600 | >83 | >83 | >83 | >83 | 83 | 9 |
| poly(styrene sulfonic acid) High Mw | >83 | >83 | >83 | >83 | 9 | 3 |
| poly(styrene sulfonic acid) Na + Mw 70000 | >83 | >83 | <83 | >83 | <0.33 | 9 |
| poly(styrene sulfonic acid) Na + Mw 500000 | >83 | >83 | >83 | >83 | 9 | 3 |
| poly(undecenoic acid, Na+) | >83 | >83 | >83 | 83 | 83 | 28 |
| poly(undecenesulfonate acid, Na~),- | >83 | >83 | 3 | 9 | 3 | 28 |
| poly(undecenesulfate, Na+) | >83 | >83 | 1 | 1 | <0.33 | <0.31~ |
| poly(undecenephosphate, Na+)** | >83 | >83 | >83 | >83 | >83 | >83 |
| poly(undecenoic acid-co-undecenesulfate, Na.+) | ~83 | >83 | 9 | 1 | 1 | 1 |
| poly(undecenoic acid-co-undecenesulfate, Na+) | >83 | >83 | 28 | 3 | 3 | 3 |
| poly(monodecyl maleic acid, Na+) | >83 | >83 | 9 | 28 | 28 | 28 |
| poly(styrenesulfonic acid-co-maleic acid, Na+) | >83 | >83 | >83 | >83 | 28 | >83 |
| poly(styrene sulfonate, Na+) Mw 1800 | >83 | >83 | 28 | 83 | 83 | 83 |
| poly(styrene sulfonate, Na+) Mw 8000 | >83 | >83 | <83 | >83 | 83 | >83 |
| poly(styrene sulfonate, Na+) Mw 220000 | >83 | >83 | <83 | >83 | 9 | 28 |
| poly(styrene sulfonate, Na+) Mw 400000 | >83 | >83 | <83 | >83 | 9 | 9 |

TABLE 1-continued

| polymer | Bacterial species* | | | | | |
|---|---|---|---|---|---|---|
| | 1 | 2 | 3 | 4 | 5 | 6 |
| poly(styrene sulfonate, Na$^+$) Mw 780000 | >83 | >83 | >83 | 83 | 28 | 28 |
| poly(styrene sulfonate, Na$^+$) Mw 1132000 | >83 | >83 | 83 | >83 | 83 | 28 |
| poly(styrene sulfonate, Na$^+$) Mw = 35,000 | >83 | >83 | >83 | >83 | 1 | 83 |
| polyvinylsulfate potassium | >83 | >83 | >83 | >83 | 28 | >83 |
| poly(acrylic acid) (Mw = 450,000) | >83 | >83 | >83 | >83 | >83 | >83 |
| sodium dodecyl sulfate '~' | >83 | >83 | 28 | 28 | 28 | 9 |
| poly(vinyl phosphonic acid), | >83 | >83 | >83 | >83 | >83 | >83 |
| poly(methylvinyl ether-co-maleic acid) | >83 | >83 | >83 | >83 | >83 | >83 |
| poly(anetholesulfonic acid, Na$^+$) | >83 | >83 | >83 | >83 | >83 | >83 |
| poly(acrylic acid-co-maleic acid) Na$^+$ | >83 | >83 | >83 | >83 | >83 | >83 |
| poly(acrylic acid-co-maleic acid) Na$^+$ | >83 | >83 | >83 | >83 | >83 | >83 |

*Bacterial species: 1 = *E. coli*; 2 = *E. Faecium*; 3 = *S. sanguis*; 4 = *S. pneumoniae*; 5 = *N. meningitidis*; 6 = *Branhamella catarrhalis*

While this invention has been particularly shown and described with reference preferred embodiments thereof, it will be understood by those skilled in the art that various changes in form and details may be made therein withou departing from the scope of the invention encompassed by the appended claims.

What is claimed is:

1. A method of treating a bacterial infection in a patient, comprising administering to the patient a therapeutically effective amount of a polymer selected from the group consisting of poly(undecenesulfate), poly(undecenephosphate), poly(undecenesulfonate), poly(styrenesulfonate, poly(undecenoic acid), poly(undecenoic acid-co-undecenesulfate) and poly(mono-$C_2$–$C_{12}$-alkylmaleic acid).

2. The method of claim 1 wherein the bacterial infection is an infection by a bacterial species selected from the group consisting of Neisseria species and Moraxella species.

3. The method of claim 2 wherein the bacterial infection is an infection by *Neisseria meningitidis* or *Moraxella catarrhalis*.

4. The method of claim 1 wherein the bacteria infection is an infection by *Streptococcus sanguis* and the polymer which is administered is poly(styrene sulfonate), poly (undecensulfate) or poly(undecensulfonate).

5. The method of claim 4 wherein the polymer is poly (styrene sulfonate, Na$^+$).

6. The method of claim 5 wherein the polymer has a molecular weight less than about 700,000 daltons.

7. The method of claim 6 wherein the polymer has a molecular weight less than about 500,000 daltons.

8. The method of claim 7 wherein the polymer has a molecular weight less than about 400,000 daltons.

9. The method of claim 1 wherein the bacterial infection is an infection by *Streptococcus pneumoniae* and the polymer which is administered is poly(undecenesulfonate), poly (undecenesulfate) or poly(undecenoic acid-co-undecenesulfate).

10. The method of claim 1 wherein the bacterial infection is an infection by *Neisseria meningitidis* and the polymer which is administered is poly(styrene sulfonate), poly (undecenesulfonate), poly(undecenesulfate), poly (undecenoic acid-co-undecenesulfate) or poly(mono-$C_2$–$C_2$-alkylmaleic acid).

11. The method of claim 10 wherein the polymer is poly(monodecylmaleic acid).

12. The method of claim 1 wherein the infection is an infection by *Moraxella catarhalis*, and the polymer which is administered is poly(styrenesulfonate), poly(undecenoic acid), poly(undecenesulfate), and poly(undecenoic acid-co-undecenesulfate).

* * * * *

UNITED STATES PATENT AND TRADEMARK OFFICE
CERTIFICATE OF CORRECTION

PATENT NO.   : 6,730,295 B2
DATED        : May 4, 2004
INVENTOR(S)  : Richard Fitzpatrick and Robert H. Barker, Jr.

It is certified that error appears in the above-identified patent and that said Letters Patent is hereby corrected as shown below:

Column 7,
Lines 36-37, insert -- ) -- after "poly(styrenesulfonate".

Column 8,
Lines 9-10 and 10, delete "poly(undecensulfate)" and insert -- poly(undecenesulfate) --;
Line 29, delete "$C_2$-$C_2$-alkylmaleic acid)" and insert -- $C_2$-$C_{12}$-alkylmaleic acid) --.

Signed and Sealed this

Twenty-fourth Day of August, 2004

JON W. DUDAS
*Director of the United States Patent and Trademark Office*